US00PP25940P2

(12) United States Plant Patent
Meerow

(10) Patent No.: US PP25,940 P2
(45) Date of Patent: Sep. 22, 2015

(54) ***HIPPEASTRUM* PLANT NAMED 'ORLANDO'**

(50) Latin Name: ***Hippeastrum* Herb.**
Varietal Denomination: Orlando

(71) Applicant: The United States of America, as represented by the Secretary of Agriculture, Washington, DC (US)

(72) Inventor: Alan W Meerow, Davie, FL (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 10 days.

(21) Appl. No.: 13/987,957

(22) Filed: Sep. 18, 2013

(51) Int. Cl.
*A01H 5/02* (2006.01)

(52) U.S. Cl.
USPC ..... Plt./402

(58) Field of Classification Search
USPC ..... Plt./402
See application file for complete search history.

*Primary Examiner* — Anne Grunberg
(74) *Attorney, Agent, or Firm* — Gail E. Poulos; John D. Fado; Lesley Shaw

(57) ABSTRACT

A new and distinct aneuploid (2n=43) moderately tall *Hippeastrum* hybrid plant named 'Orlando' measuring approximately 13-14.5 cm long, approximately 14-16 cm wide laterally, approximately 17-19 cm wide dorsal-ventrally. The flowers are densely striated pink-purple approximately RHS Red Purple 66A on their upper surfaces, with a broad white RHS 155D keel.

3 Drawing Sheets

Latin name of the genus and species of the plant claimed: 'Orlando' is a new amaryllis plant that is a *Hippeastrum* Herb.

Variety denomination: The amaryllis plant claimed is of the variety denominated 'Orlando', *Hippeastrum* Herb.

BACKGROUND OF THE INVENTION

The present invention is a new and distinct complex hybrid of *Hippeastrum* Herb., commonly known as amaryllis, a member of the family Amaryllidaceae, and is henceforth referred to by the cultivar name 'Orlando'.

'Orlando' originated as a cross made by the inventor in 2001 as part of a breeding program in Miami, Fla., USA. The objectives of the breeding program are to develop new amaryllis varieties with novel floral form and coloration and heat tolerance. The female parent is a proprietary selection of the complex cross (*Hippeastrum ambiguum*×*H. papilio*)×*H. brasilianum* labeled with the breeder's code 101-5. The pollen parent is the non-patented commercial *Hippeastrum* 'Wonderland'.

The new cultivar was selected on the basis of large flowers with deep pink-purple coloration contrasted by a broad median white stripe on the tepals. Over the course of seven years of evaluation, 'Orlando' has shown excellent heat resistance, grown under ambient conditions in Orlando, Fla. under 50% shade, and resistance to Red Scorch fungus (*Staganospora curtisii*).

Asexual reproduction of the new cultivar by twin-scale cuttings taken in a controlled environment in Miami, Fla. has shown that the unique features of this new amaryllis are stable and reproduced true to type in successive generations.

SUMMARY OF THE INVENTION

The following traits have been repeatedly observed and are determined to be the unique characteristics of 'Orlando'. It is contrasted with its parents in Table 1. These characteristics in combination distinguish 'Orlando' as a new and distinct cultivar: 1) Deep cerise pink color, RHS 66A, of the tepals with very bold white, RHS 155D, stripe along keels.

TABLE 1

Comparison of *Hippeastrum* 'Orlando' and its two parent plants.

| Characteristic | 'Orlando' | Clone 101-5 | 'Wonderland' |
|---|---|---|---|
| No. scapes per season | 3 | 2 | 2 |
| Scape height (cm) | 40-65.7 | 40-55 | 40-60 |
| No. firs. per scape | 4-6 | 4 | 4 |
| Flr. color | Cerise pink and clear white | Deep pink-purple, white keels. | Pink-purple and light white |

Of the numerous commercial cultivars of amaryllis familiar to the inventor, the most similar to the new *Hippeastrum* 'Orlando' is *Hippeastrum* 'Wonderland' (unpatented), from which 'Orlando' differs by its larger flowers, the cerise pink (approximately RHS Red Purple 66A) color of the tepals, and the broader and more pronounced white, RHS 155D, stripes along the keel of the flowers.

BRIEF DESCRIPTION OF THE PHOTOGRAPHS

DETAILED BOTANICAL DESCRIPTION

The cultivar Orlando has not been observed under all possible environmental conditions. The phenotype may vary somewhat with variations in environment such as temperature, daylength and light intensity, without, however, any variance in genotype.

Color descriptions below are based on evaluations with a Minolta CR-400 colorimeter at CIE D65/2° illumination/viewer conditions. The color parameters correspond to the uniform color space CIELAB, derived from Gonnet (Journal of Horticultural Science, Volume 68, 499-510, 1993; Food Chemistry, Volume 63, 409-415, 1998). Two color coordinates, a* and b*, as well as a psychometric index of lightness, L*, are defined. The L* is a measurement of luminosity, i.e., the equivalence of each color on the gray scale, ranging from 0 (black) to 100 (white). The a* takes positive values (0 to +60) for reddish colors and negative values (0 to −60) for the greenish ones, whereas the b* takes positive values (0 to +60) for yellowish colors and negative values (0 to −60) for the bluish ones. This is much more precise and repeatable analysis of color than obtained by using color charts (Ayala-Silva and Meerow, Proc. Intl. Trop. Hort. Soc., Volume 50, 138-144, 2006). The colorimeter takes three consecutive measurements of each sample, which was repeated three times, thus each set of color coordinates obtained are means of nine measurements. Where a reasonably close match could be discerned, The R.H.S. Colour Chart (Royal Horticultural Society, London, England, 1966) is also referenced.

TABLE 2

Colorimeter readings under the CIELAB color space for various locations on the flowers of *Hippeastrum* hybrid 'Orlando'. See text for explanation of the values.

Figure 1B:
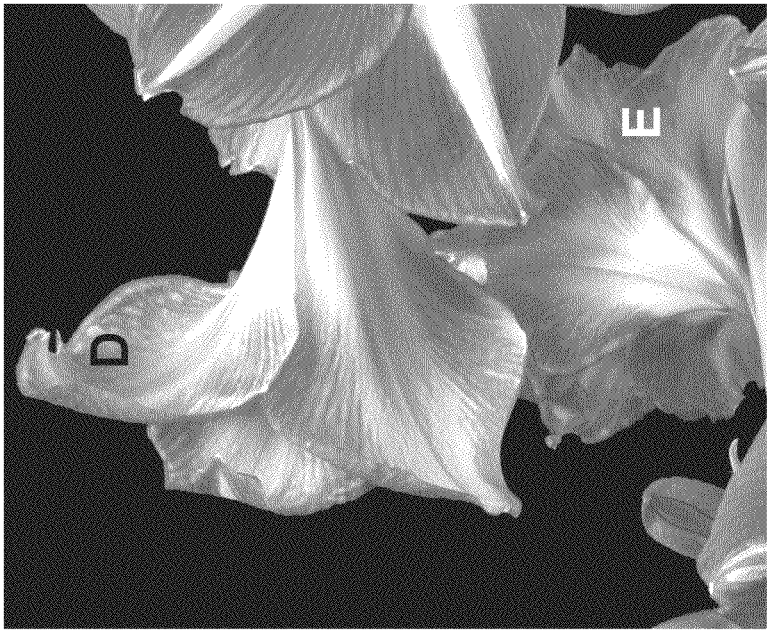
FIGS. 1A and 1B are gray scale pictures of the flowers of *Hippeastrum* hybrid 'Orlando' showing the locations of colorimeter readings in Table 2 below.
Figure 1A:
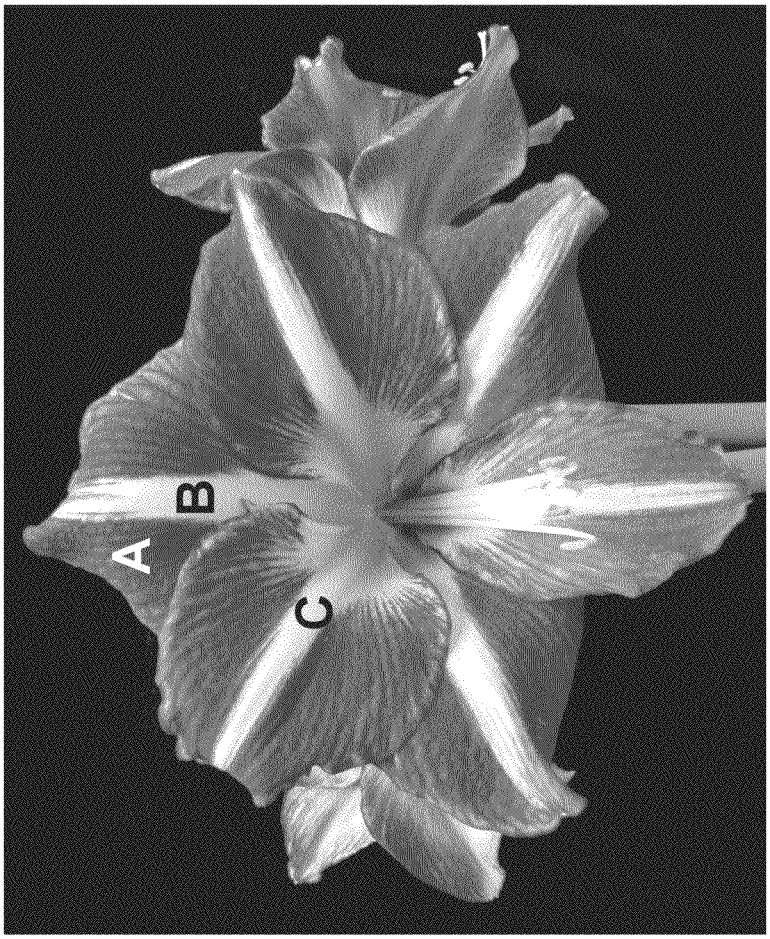
Figure 2:
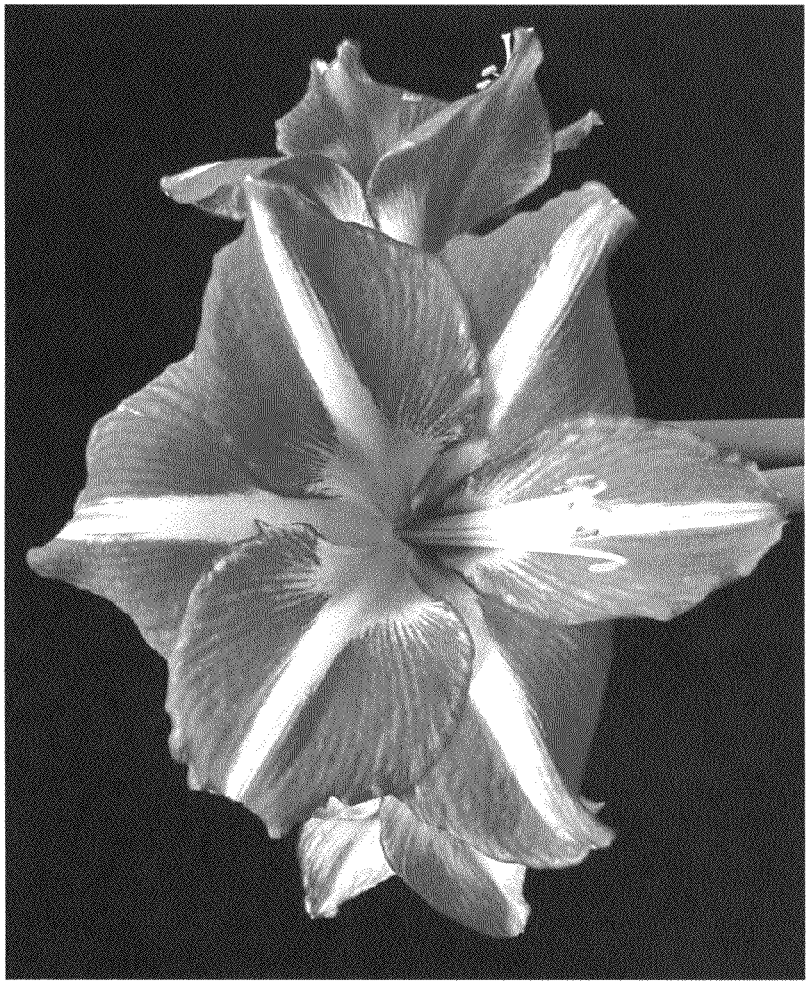
FIGS. 2 and 3 are photographs of the flower of *Hippeastrum* hybrid 'Orlando'.
Figure 3:
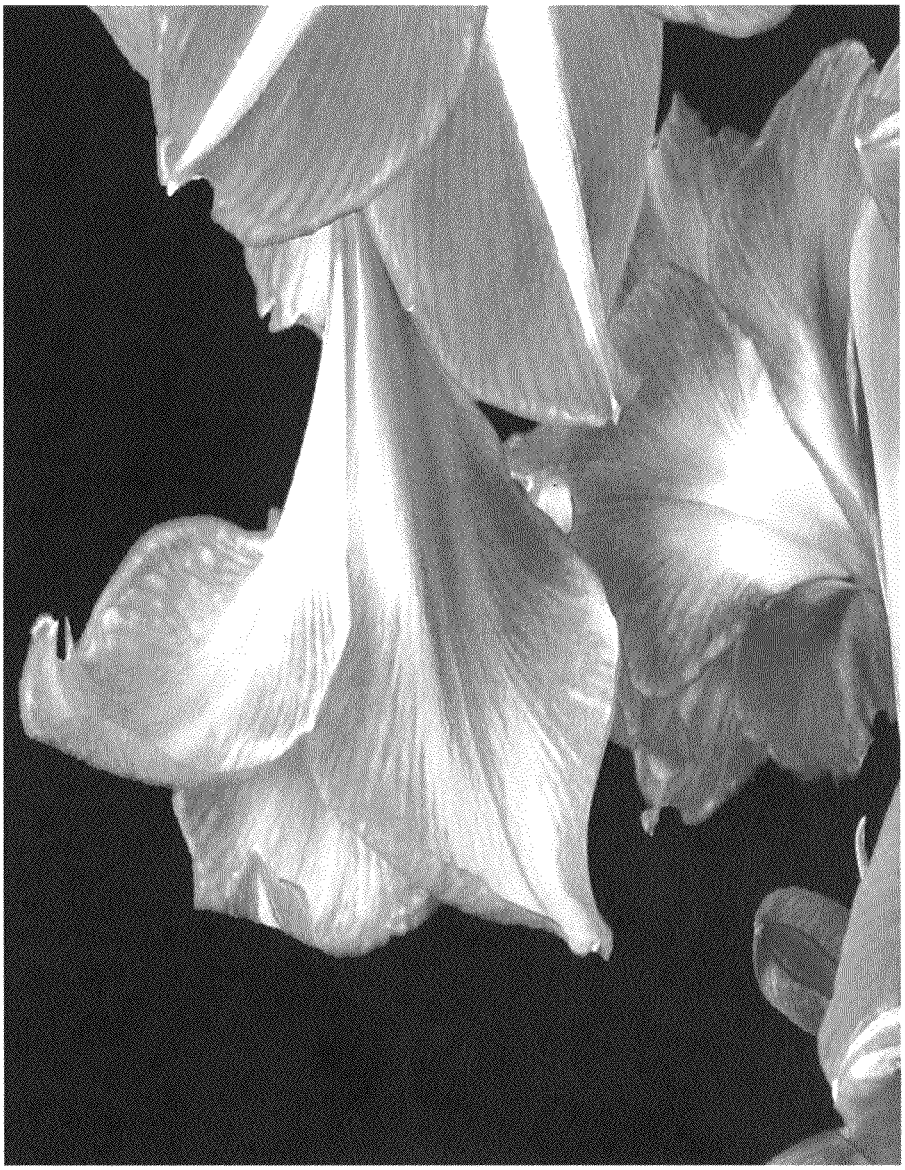

| Location (see FIG. 1) | | L*(C) | a*(C) | b*(C) |
|---|---|---|---|---|
| A | MEAN | 27.1 | 48.5 | 22.36 |
| | STDEV | 0.9 | 13.1 | 6.331 |
| B | MEAN | 81.54 | −0.77 | 5.79 |
| | STDEV | 0.38 | 0.51 | 0.16 |
| C | MEAN | 83.07 | −0.47 | 6.28 |
| | STDEV | 0.67 | 0.19 | 0.47 |
| D | MEAN | 27.78 | 51.19 | 22.42 |
| | STDEV | 0.93 | 1.09 | 4.47 |
| E | MEAN | 29.38 | 50.44 | 21.37 |
| | STDEV | 1.43 | 2.06 | 3.57 |

Botanical classification: *Hippeastrum* hybrid cultivar Orlando.

Parentage: The female parent is a proprietary selection of the complex cross (*Hippeastrum ambiguum*×*H. papilio*)×*H. brasilianum* labeled with the breeder's code 101-5. The male or pollen parent is the non-patented commercial *Hippeastrum* 'Wonderland'.

Propagation:

*Type.*—Twin-scale cuttings (division of the mother bulb into vertical segments and twin-scale units).

*Time to initiate roots, summer.*—About 30 days at temperatures of about 30° C.

*Time to initiate roots, winter.*—About 40 days at temperatures of about 22° C.

*Time to develop roots, summer.*—About 65 days at temperatures of about 30° C.

*Time to develop roots, winter.*—About 90 days at temperatures of about 22° C.

Plant description:

*Appearance.*—Perennial herbaceous amaryllis. Upright and clumping growth habit, moderately dwarf.

*Crop time.*—From bulb scale cuttings, about two years are required to produce a finished, flowering plant in about 15 to 20-cm container.

*Vigor.*—Moderately vigorous.

*Plant height.*—About 60 cm.

*Plant spread.*—About 80 cm.

Roots: White; numerous; fine and fibrous to moderately thick and fleshy; produced from basal plate of bulb; freely branching.

Bulb:

*Diameter.*—Approximately 6-11 cm.

*Circumference.*—Approximately 19-35 cm.

*Shape.*—Ovoid.

*Color.*—RHS 149A; tunic, RHS 165A.

*Offsets produced per year.*—About three to five offsets per bulb.

Foliage description.

*Arrangement.*—Distichous.

*Quantity.*—About 4-6 per bulb (up to 9 late in the season).

*Length, mature leaves.*—Approximately 35-45 cm early in season, approximately 65-72 cm late in season.

*Width, mature leaves.*—About 4.5-6.5 cm.

*Shape.*—Lorate.

*Apex.*—Acute.

*Margin.*—Entire.

*Texture.*—Coarse; glabrous.

*Color.*—Young foliage, upper surface: RHS 144A. Young foliage, lower surface: RHS 144B. Mature foliage, upper surface: L*(C)=37.57, a*(C)=−13.41, b*(C)=18.08. Mature foliage, lower surface: L*(C)=44.34, a*(C)=−15.71, b*(C)=24.09.

Flower description:

*Appearance.*—Wide spreading funnel-shaped single flowers arranged in umbels borne on a leafless scape. Corolla and calyx similar (tepals), three-parted and fused at the base: Freely flowering, typically four open flowers per scape and about eight to 12 flowers and flower buds per plant. Flowers last about three or four days each. Flowers persistent. Flowers held perpendicular to the scape.

*Flowering response.*—Plants flower in the spring. Plants typically flower about March 10 to April 30 in Miami, Fla.

*Fragrance.*—Not detected.

*Scape.*—Length: approximately 40-65.7 cm. Diameter: About 1 cm. Appearance/aspect: Leafless; upright; not fasciated, hollow. Strength: Moderate. Texture: Smooth. Color (apex): L*(C)=45.01, a*(C)=−0.08, b*(C)=14.76; color (base): L*(C)=39.02, a*(C)=9.44, b*(C)=10.76.

*Pedicel.*—Approximately 5.5-8.0 cm long.

*Flower length.*—Approximately 13-14.5 cm.

*Flower diameter.*—Approximately 14-16 cm.

*Flower depth (height).*—Approximately 17-19 cm.

*Flower buds.*—Length: about 4 cm. Width: about 1 cm. Shape: Oblanceolate. Color: close to RHS Yellow-Green 144B in lower half, RHS Red Purple 66A in upper half. Rate of flower bud opening: about 2 days each, all flowers opening in about 8-10 days.

*Tepals.*—Number: six, in two whorls of 3. Fused and forming tube in proximal approximately 2 cm. Tube green, L*(C)=57.13, a*(C)=−13.95, b*(C)=32.79. Outer whorl: Length: approximately 12.0-12.5 cm. Width: approximately 7.9-9.0 cm. Shape: broadly ovate. Apex: apiculate. Margin: entire. Texture: Smooth; petals appear luminous and crystalline. Color: upper surface: striated RHS Red Purple 66A (Table 2), green (RHS 144C) at base, with median pure white keels (RHS 155D) 1.3-1.5 cm wide; lower surface striations more diffuse, with white (RHS 155D) background, white (RHS 155D) towards middle, green (RHS 144C) towards base, keel suffused with green (RHS 144C) near apex and on either side in the lower ½. Inner whorl — Length of lateral: approximately 11.5-12.0 cm, ventral: approximately 12.5-12.9 cm; width of lateral: approximately 6.5-6.9 cm, ventral: approximately 4.8-5.0 cm. Shape: ovate, the ventral tepal narrower. Apex: apiculate. Margin: entire. Color (Table 2): striated RHS Red Purple RHS 66A, green RHS 144C at base, with median pure white keels RHS 155D, approximately 1.3-1.5 cm wide; lower surface striations more diffuse, with white RHS 155D background, white RHS 155D towards middle, green RHS 144C towards base, keel suffused with green RHS 144C near apex and on either side in the lower ½.

*Throat.*—Green RHS 144C, with short lacinate fimbrae.

*Reproductive organs.*—Androecium: Stamen number: Six. Length: approximately 8.9-10.0 cm; filaments white RHS 155D in their distal ¾, green RHS 144C in their proximal ¼. Anther shape: elliptic. Anther size: About 7 mm. Anther color: white RHS 155D. Pollen amount: moderate. Pollen color: yellow RHS 3D. Gynoecium: Pistil number: one. Pistil length: About 11.5-12 cm. Stigma shape: tri-lobed. Stigma width: about 6-7 mm. Stigma color: white RHS 155D. Style color: white RHS 155D for ¾ length, with faint pink RHS 66A stippling below the stigma, green RHS 144C in lower ¼. Ovary shape: ellipsoid, ovary length: approximately 21-24 mm, ovary width: approximately 8-10 mm, ovary color: RHS Green 141C.

*Fruit.*—A loculicidal capsule, about 2 cm long, about 3 cm wide, papery at maturity.

*Seed.*—Seed flattened, obliquely winged, dark brown RHS 200A, about 10 cm long, about 0.5 cm wide.

Chromosome number: 2n=43. Plant is aneuploid (4n−1).

Disease resistance: Plants of the new amaryllis appear resistant to Red Scorch Fungus (*Staganospora curtisii*).

Heat tolerance: Plants of the new amaryllis have demonstrated good tolerance to high temperatures about 30 to 35° C.

I claim:

1. A new and distinct cultivar of amaryllis (genus *Hippeastrum*) named 'Orlando', as illustrated and described.

* * * * *